United States Patent [19]

Moreau et al.

[11] Patent Number: 4,894,231

[45] Date of Patent: Jan. 16, 1990

[54] THERAPEUTIC AGENT DELIVERY SYSTEM

[75] Inventors: Jacques-Pierre Moreau, Upton; Judith P. Kitchell, Newton, both of Mass.

[73] Assignee: Biomeasure, Inc., Hopkinton, Mass.

[21] Appl. No.: 78,534

[22] Filed: Jul. 28, 1987

[51] Int. Cl.$^4$ .......................... A61F 2/00; A61K 9/14
[52] U.S. Cl. .................... 424/426; 424/422; 424/484; 424/502; 427/2; 427/3
[58] Field of Search ............... 424/484, 426, 422, 502; 427/2, 3

[56] References Cited

U.S. PATENT DOCUMENTS

| | | | |
|---|---|---|---|
| 3,279,996 | 10/1966 | Long et al. | 424/422 |
| 3,854,480 | 12/1974 | Zaffaroni | 128/260 |
| 3,944,064 | 3/1976 | Bashaw et al. | 424/422 X |
| 4,159,322 | 6/1979 | Cloyd | 424/181 |
| 4,230,686 | 10/1980 | Schopflin et al. | 424/422 |
| 4,351,337 | 9/1982 | Sidman | 424/426 X |
| 4,622,244 | 11/1986 | Lapka et al. | 427/213.32 |

OTHER PUBLICATIONS

Rankin, *Chimicaoggi*, p. 37 (10/86).

*Primary Examiner*—Thurman K. Page
*Attorney, Agent, or Firm*—Fish & Richardson

[57] ABSTRACT

A therapeutic agent delivery system that includes a biodegradable polymer and a therapeutic agent, the delivery system being coated with a barrier substance that decreases the quantity of the agent released from the system, compared to the quantity of the agent released from a system not coated with the substance, in the forty-eight hours subsequent to the parenteral injection or implantation of the system into a living person or animal.

9 Claims, No Drawings

THERAPEUTIC AGENT DELIVERY SYSTEM

BACKGROUND OF THE INVENTION

This invention relates to the release of therapeutic agents from delivery systems.

Biodegradable polymers containing a therapeutic agent are often used to administer the agent to a patient. Generally the release results from the dissolution of the polymer and from the diffusion of the agent through pores and channels in the matrix.

SUMMARY OF THE INVENTION

In general, the invention features, in one aspect, a therapeutic agent delivery system that includes a biodegradable polymer and a therapeutic agent, the delivery system being coated with a barrier substance that decreases the quantity of the agent released from the system, compared to the quantity of the agent released from a system not coated with the substance, in the forty-eight hours subsequent to the parenteral injection or implantation of the matrix into a living person or animal.

In preferred embodiments, the barrier substance is silicone oil that has a viscosity of between $10^2$ centipoise (cp) and $10^4$ cp.

In another aspect, the invention features a method of providing a coated therapeutic agent delivery system that includes a biodegradable polymer and a therapeutic agent, the method including the steps of coating the delivery system with a barrier substance, and treating the delivery system to remove some but not all of the barrier substance.

In some preferred embodiments, the barrier substance is a silicone oil, and the treating includes washing the delivery system with a solvent that removes some of the barrier substance.

Delivery systems consisting of a biodegradable polymer and a therapeutic agent are made in a variety of ways, e.g., solvent casting, coacervation procedures, or dispersion. When the former procedure is used, the agent is dispersed as small particles throughout the system. The small particles are irregularly shaped with small jagged edges; the edges may extend to the surface of the system, or may cause cracks in the system that extend to the surface. When such a system is inserted into a patient, a dose of agent larger than the desired dosage is released from the system through these surface contacts.

Delivery systems prepared by coacervation consist of an aggregate of agent surrounded by the polymer. The large crystal may have jagged edges extending to the surface, or may cause cracks that extend to the surface. Accordingly, the initial burst of agent problem is also present in these systems.

Coating the surface of the delivery system with a barrier substance limits the release of agent from the delivery system for the initial one or two day period following administration, thus decreasing the agent's possibly deleterious side effects that can result from initial bursts of high agent release. In addition, because the initial quantity of agent released is limited, more agent remains in the system allowing for a longer effective period of use for the matrix.

The delivery system is easy to use and inexpensive to make. Moreover, because of the coating, the delivery system has superior handling properties in that it does not clump together when in powdered form.

Other features and advantages of the invention will be apparent from the following description of the preferred embodiment, and from the claims.

DESCRIPTION OF THE PREFERRED EMBODIMENT

We now describe the structure, method of preparation, and use of the preferred embodiment.

Structure

The delivery system employs a biodegradable polymer containing a therapeutic agent. The system is coated with a barrier substance; the barrier substance, when the system is introduced into a vertebrate (preferably a mammal such as a human or domestic animal such as a dog or cow) decreases the initial burst of therapeutic agent from the system.

A biodegradable polymer is a polymer which slowly dissolves or degrades in a physiological environment into low molecular weight molecules that are then transported from the site. Types of biodegradable polymers suitable for use in a delivery system include polyanhydrides, partially crosslinked proteins, polylactic acid, polyglycolic acid, polyorthoesters, polysaccharides, polaxomers, hydroxypropylcellulose, polyethyleneglycol, copolymers of lactide and glycolide, and carboxymethylcellulose. Some representative examples of poly(lactide/glycolide) biodegradable polymers are described by Kitchell & Wise, 112 Methods In Enzymology 436 (1985).

The delivery systems of the invention preferably are injected or implanted parenterally into an animal or a human patient. Where the system is to be injected, it should be small enough in diameter to fit through the needle tip of the syringe. The preferred delivery systems for injection have an average size of 500 microns or less (more preferably 250 microns or less, most preferably 100 to 200 microns); rod shaped systems of 1–10 mm diameter, which generally are long and slender, may also be used.

The term therapeutic agent, as used herein, means any agent used to treat or prevent any disease or disorder of the body. Representative agents include hormones (and hormone fragments and analogues), e.g., testosterone, luteinizing hormone-releasing hormone (LHRH); diuretics, e.g., chlorothiazide; anti-inflammatories; pain killers, e.g., morphine; antibiotics, e.g., tetracycline; antipsychotic drugs; anticancer drugs, e.g., methotrexate, actinomycin D, vinblastine, and cytosine arabinoside; vaccines; and antiarthritic drugs, e.g., ibuprofen and flurbiprofen.

One of the roles of the barrier substance is to limit the initial burst of therapeutic agent from the delivery system. The substance should not affect the long term sustained release of the agent, and therefore should be a substance that dissolves or wears off the surface of the system within a short period of time after injection; preferably, the barrier substance should dissipate within 5 days after injection, more preferably within 2 days after injection. The substance should be non-toxic, non-irritating, non-sensitizing, and hydrophobic. Preferably the substance is on the GRAS list or is USP approved.

Examples of suitable barrier substances include paraffins, beeswax, and, preferably, silicone oils.

Silicone oils are organo-siloxane polymers based on a structure consisting of alternating silicon and oxygen atoms with organic groups (R) attached to the silicon atoms:

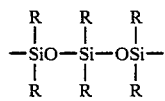

Typical silicone oils include those in which R is a lower alkyl group having six or less carbons, e.g., a methyl group. Silicone oils have a viscosity of between 1 cp and $10^6$cp. The more preferred silicone oils have a viscosity of between $10^2$ cp and $10^4$ cp; most preferably the silicone oils have a viscosity of between 500 cp and 2000 cp. Representative examples of silicone oils include Union Carbide dimethylpolysilicone #L-45 (viscosity 1000 cp), Dow Corning medical grade silicone oil #360, Aldrich silicone oil (catalogue no. 17,563-3), and Aldrich silicone oil (catalogue no. 14,615-3).

The delivery system can comprise up to 70% agent by weight. If a system comprises greater than 70% agent by weight, the mechanical properties of the system may be adversely affected.

Method of Preparation

The uncoated delivery system can be prepared by standard solvent casting techniques. In general, the polymer is dissolved in an organic solvent and the therapeutic agent added. The solution or suspension is then poured into a suitable mold and the solvent evaporated to yield a polymer agent combination. Alternatively, the agent can be dispersed with the polymer without solvent.

The delivery systems can also be prepared by coacervation procedures, such as those described by Lapka et al., U.S. Pat. No. 4,622,244, which is hereby incorporated by reference.

The uncoated delivery system of choice (generally in the form of a powder) is placed in a flask and covered with a silicone oil such as Union Carbide dimethylpolysilicone #L-45. The thickness of the organic solvent capable of dissolving silicone oil. The thicker the coating, the more limited the initial burst of release of agent from the system. The powder is dried under a stream of nitrogen gas, and then under vacuum for 24 hours.

Alternate methods of coating include spraying a thin coat of silicone oil onto the powder; and mixing the powder in a solvent in which the barrier substance has been dissolved and then evaporating off the solvent.

Where the delivery system is a powder made up of particles having an average size of 100-200 microns, following coating each particle should be 0.05%-10% (more preferably 0.1%-2%) silicone oil by weight. The amount of silicone oil present can be calculated by first conducting an elemental analysis of the powder to determine the amount of silicon present; knowing the percentage of silicon in the oil, the amount of oil can then be determined.

Use

The delivery systems containing the standard dosage of the selected therapeutic agent and coated with a barrier substance are injected, implanted, or otherwise inserted parenterally into a patient. The barrier substance limits the initial burst of the agent from the polymer; over a short period of time, the barrier substance wears off of the surface of the system, allowing the system to release the desired dosage over a sustained period of time.

A comparison of the initial quantity of agent released from the coated delivery system and an uncoated delivery system can be made by (1) injecting or implanting equal amounts (uncoated weight) of the systems into different animals; and (2) either determining the levels of agent in the animal's blood after 48 hours, or measuring the biological effect that the agent induces (e.g., for delivery systems that release LHRH, the level of testosterone in serum is measured, that level being directly correlated to the amount of LHRH released). It is understood that, although it is most preferred that the initial release be limited to the desired dosage of the agent, the advantages of the invention, such as reducing side effects of large dosages of the agent, are achieved if the initial release is reduced by as little as ten percent (more preferably twenty percent).

Other embodiments are within the following claims.

We claim:

1. A therapeutic agent delivery system comprising a biodegradable polymer and a therapeutic agent, said delivery system being coated with a barrier substance that decreases the quantity of said agent released from said system, compared with the quantity of said agent released from a said system not coated with said barrier substance, in the forty-eight hours subsequent to the parenteral injection or implantation of said system into a living person or animal, said barrier substance being selected from the group consisting of a paraffin, beeswax, or a silicone oil and being adapted to dissipate from said delivery system within a short time period after said injection or implantation.

2. The coated therapeutic agent delivery system of claim 1 wherein said barrier substance is a silicone oil.

3. The coated therapeutic agent delivery system of claim 2 wherein said silicone oil has a viscosity of between $10^2$ centipoise and $10^4$ centipoise.

4. The coated therapeutic agent delivery system of claim 2 wherein said silicone oil has a viscosity of between 500 centipoise and 2000 centipoise.

5. A method of providing a coated therapeutic agent delivery system comprising
   coating a therapeutic agent delivery system comprising a biodegradable polymer and therapeutic agent with a barrier substance that decreases the quantity of said agent released from said system, compared with the quantity of said agent released from a said system not coated with said substance, in the forty-eight hours subsequent to the parental injection or implantation of said system into a living person or animal, said barrier substance being selected from the group consisting of a paraffin, beeswax, or a silicone oil; and
   treating said delivery system to remove some but not all of said barrier substance.

6. The method of claim 5 wherein said barrier substance is a silicone oil.

7. The method of claim 5 wherein said treating comprises washing said delivery system with a solvent.

8. The coated delivery system of claim 1 wherein said short period is 5 days or less.

9. The coated delivery system of claim 8 wherein said short period is 2 days or less.

* * * * *

UNITED STATES PATENT AND TRADEMARK OFFICE
CERTIFICATE OF CORRECTION

PATENT NO. : 4,894,231

DATED : January 16, 1990

INVENTOR(S) : Jacques-Pierre Moreau, et al

It is certified that error appears in the above-identified patent and that said Letters Patent is hereby corrected as shown below:

Column 3, line 41, after "the", insert --coating can be adjusted by rinsing with hexane or other--.

Signed and Sealed this

Fifteenth Day of January, 1991

Attest:

HARRY F. MANBECK, JR.

*Attesting Officer*  *Commissioner of Patents and Trademarks*